(12) United States Patent
Faulhaber

(10) Patent No.: US 12,178,715 B2
(45) Date of Patent: *Dec. 31, 2024

(54) EXPANDABLE FUSION DEVICES AND METHODS OF INSTALLATION THEREOF

(71) Applicant: GLOBUS MEDICAL, INC., Audubon, PA (US)

(72) Inventor: Kurt Faulhaber, Cape Coral, FL (US)

(73) Assignee: Globus Medical, Inc., Audubon, PA (US)

( * ) Notice: Subject to any disclaimer, the term of this patent is extended or adjusted under 35 U.S.C. 154(b) by 157 days.

This patent is subject to a terminal disclaimer.

(21) Appl. No.: 17/933,871

(22) Filed: Sep. 21, 2022

(65) Prior Publication Data

US 2023/0016103 A1    Jan. 19, 2023

Related U.S. Application Data

(63) Continuation of application No. 16/736,288, filed on Jan. 7, 2020, now Pat. No. 11,484,414, which is a continuation of application No. 15/869,260, filed on Jan. 12, 2018, now Pat. No. 10,548,743, which is a
(Continued)

(51) Int. Cl.
*A61F 2/44* (2006.01)
*A61F 2/30* (2006.01)
*A61F 2/46* (2006.01)

(52) U.S. Cl.
CPC ............ *A61F 2/4455* (2013.01); *A61F 2/447* (2013.01); *A61F 2/4611* (2013.01); *A61F 2002/30487* (2013.01); *A61F 2002/305* (2013.01); *A61F 2002/30556* (2013.01); *A61F 2002/30593* (2013.01); *A61F 2002/30836* (2013.01); *A61F 2002/30843* (2013.01); *A61F 2002/3093* (2013.01); *A61F 2002/4627* (2013.01)

(58) Field of Classification Search
CPC ................. A61F 2002/4475; A61F 2002/4627
USPC ...................... 606/246–249; 623/17.11–17.16
See application file for complete search history.

(56) References Cited

U.S. PATENT DOCUMENTS

| | | |
|---|---|---|
| 4,349,921 A | 9/1982 | Kuntz |
| 4,599,086 A | 7/1986 | Doty |
| 4,863,476 A | 9/1989 | Shepperd |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Eduardo C Robert
*Assistant Examiner* — Tara Rose E Carter

(57) ABSTRACT

Exemplary embodiments of apparatuses and methods of an expandable fusion device are provided. In one embodiment, an intervertebral implant can be provided, having a first endplate having an upper surface and a lower surface, a second endplate having an upper surface and a lower surface. A first side wall extends from the first endplate and a second side wall extends from the second endplate and are configured to engage one another to provide a selective variable height between the first endplate and the second endplate. The first side wall and the second side wall form a substantially hollow portion substantially enclosed by the first endplate, second endplate and the side walls. The substantially hollow portion is configured to receive bone growth inducing material.

18 Claims, 17 Drawing Sheets

Related U.S. Application Data continuation of application No. 14/571,773, filed on Dec. 16, 2014, now Pat. No. 9,901,459.

(56) References Cited

U.S. PATENT DOCUMENTS

| | | |
|---|---|---|
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | Jimenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | JImenez et al. |
| 9,532,883 B2 | 1/2017 | McLuen et al. |
| 9,622,878 B2 | 4/2017 | Grotz |
| 9,901,459 B2 * | 2/2018 | Faulhaber ............. A61F 2/4455 |
| 10,548,743 B2 * | 2/2020 | Faulhaber ............. A61F 2/4611 |
| 11,484,414 B2 * | 11/2022 | Faulhaber ............... A61F 2/447 |
| 2002/0045945 A1 | 4/2002 | Liu |
| 2002/0068976 A1 | 6/2002 | Jackson |
| 2002/0068977 A1 | 6/2002 | Jackson |
| 2003/0074063 A1 * | 4/2003 | Gerbec ................. A61F 2/4611 |
| | | 623/16.11 |
| 2003/0176926 A1 | 9/2003 | Boehm et al. |
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |

(56) References Cited

U.S. PATENT DOCUMENTS

| | | |
|---|---|---|
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1* | 2/2010 | Valdevit ............ A61F 2/447 623/17.16 |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

\* cited by examiner

EXPANDABLE FUSION DEVICES AND METHODS OF INSTALLATION THEREOF

CROSS-REFERENCE TO RELATED APPLICATIONS

This application is a continuation of U.S. patent application Ser. No. 16/736,288 filed on Jan. 7, 2020, which is a continuation of U.S. patent application Ser. No. 15/869,260, filed on Jan. 12, 2018 (published as U.S. Pat. Pub No. 2018-0133025), which is a continuation of U.S. patent application Ser. No. 14/571,773, filed on Dec. 16, 2014 (now U.S. Pat. No. 9,901,459), all of which are incorporated herein by reference in their entireties for all purposes.

FIELD OF THE DISCLOSURE

The present disclosure relates to exemplary embodiments of systems, apparatuses and methods for promoting an intervertebral fusion, and more particularly, to exemplary embodiments of an expandable fusion device capable of being inserted between adjacent vertebrae to facilitate a fusion process.

BACKGROUND INFORMATION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of devices and methodologies in the art for accomplishing intervertebral fusion. These include fusion devices which include a cage or other implant mechanism, which can be packed with bone and/or bone growth inducing substances. These devices are implanted between adjacent vertebral bodies in order to fuse the vertebral bodies together, alleviating the associated pain.

However, there are drawbacks associated with these devices and methodologies. For example, present methods for installing a fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum height that can allow for bone growth inducing material within the fusion device to allow for fusion of the implant with the vertebral bodies. In addition, there is a need for providing secured fusion devices such that additional supplemental fixation may not be necessary, or at least optional.

At least one of the objects of the exemplary embodiments of the present disclosure is to reduce or address the deficiencies and/or limitations of the prior art procedures and apparatuses described herein above, by providing an intervertebral implant that does not suffer from these deficiencies.

SUMMARY OF EXEMPLARY EMBODIMENTS OF THE PRESENT DISCLOSURE

At least some of the above described problems can be addressed by exemplary embodiments of the apparatuses and methods according to the present disclosure. For example, using such exemplary embodiments, it is possible to provide an expandable fusion device capable of being installed inside an intervertebral disc space to maintain normal disc spacing and restore spinal stability, thereby facilitating an intervertebral fusion, and providing a secured expandable fusion device so that posterior fixation may not be necessary.

In some exemplary embodiments, an intervertebral implant can be provided, comprising a first endplate having an upper surface and a lower surface, a second endplate having an upper surface and a lower surface, and a side wall disposed between the first endplate and the second endplate and configured to have a selective height between the first endplate and the second endplate, wherein the side wall forms a substantially hollow portion substantially enclosed by the first endplate, second endplate and the side wall, and wherein the substantially hollow portion is configured to receive bone growth inducing material.

The side wall can comprise a first side wall extending from the lower surface of the first endplate, and a second sidewall extending from the upper surface of the second endplate. The intervertebral implant can further comprise an engagement mechanism for engaging the first sidewall to the second sidewall and configured to provide a selective height of the sidewall between the first endplate and the second endplate. The engagement mechanism can comprise a plurality of rails along a length of an outer portion of the first sidewall from a proximal end to a distal end and a plurality of grooves along a length of an inner portion of the second sidewall from a proximal end to a distal end for selective engagement with the one or more rails. The first sidewall can comprise a wall extending from a first side, a second opposing side and a distal end of the first endplate, and the second sidewall comprises a wall extending from a first side, a second opposing side and a distal end of the second endplate.

The intervertebral implant can further comprise an opening between a proximal end of the first endplate and a proximal end of the second endplate configured to allow placement of an implant holder therein. The intervertebral implant can further comprise an implant holder interface provided along an outer portion of the second sidewall at opposing ends and configured to secure the intervertebral implant to an implant holder. The intervertebral implant can further comprise an end cap interface provided along an outer portion of the second sidewall at opposing ends. The intervertebral implant can further comprise an end cap secured to the end cap interface of the second sidewall engaging a wall of the lower surface of the first endplate and the upper surface of the second endplate, the end cap configured to prevent displacement of the first endplate with respect to the second endplate. The end cap can seal the opening between the proximal end of the first endplate and the proximal end of the second endplate.

The intervertebral implant can further comprise a securing mechanism in the end cap for securing the intervertebral implant to a vertebral body above the first endplate and a vertebral body below the second endplate. The securing mechanism can further comprise a drive plate provided within the end cap, the drive plate comprising a first spike configured to advance from the drive plate and engage with a vertebral body for securing the intervertebral implant to a vertebral body above the first endplate, and a second spike configured to advance from the drive plate and engage with a vertebral body for securing the intervertebral implant to a vertebral body below the second endplate. The first and second spikes can be configured to advance as a driver engaged with the drive plate is turned.

The substantially hollow portion can be configured for placement of a cam, and configured to displace and engage the engagement mechanism as the cam is rotated. The intervertebral implant can further comprise one or more slots between the upper surface of the first endplate to the lower surface of the first endplate configured to allow fusion of bone growth inducing material within the intervertebral implant and a vertebral body above the first endplate, and one or more slots extending from the upper surface of the second endplate to the lower surface of the second endplate configured to allow fusion of bone growth inducing material within the intervertebral implant and a vertebral body below the second endplate. The upper surface of the first endplate can comprise texturing for engaging with a vertebral body and a lower surface of the second endplate can comprise texturing for engaging with a vertebral body.

In some exemplary embodiments, an intervertebral implant can be provided, comprising an upper endplate having a proximal end, a distal end, a first side and an opposing second side, a lower endplate having a proximal end, a distal end, a first side and an opposing second side, a first sidewall extending along a periphery of the first side, distal end and second side of the upper endplate towards the lower endplate, a second sidewall extending along a periphery of the first side, distal end and second side of the lower endplate towards the upper endplate, and an engagement mechanism for selective engagement of the first sidewall with the second sidewall configured to provide a selective distance between the upper endplate and the lower endplate, wherein the upper endplate, lower endplate, first sidewall and second sidewall partially enclose a substantially hollow portion configured to receive bone growth inducing material therein.

The intervertebral implant can further comprise an end cap secured to the second sidewall engaging a wall of the upper endplate and the lower endplate, the end cap configured to retain a selected height between the upper endplate and the lower endplate and seal an opening between the proximal ends of the upper endplate and the lower endplate. The intervertebral implant can further comprise one or more slots in the upper endplate configured to allow fusion of bone growth inducing material within the intervertebral implant and a vertebral body above the upper endplate, and one or more slots in the lower endplate configured to allow fusion of bone growth inducing material within the intervertebral implant and a vertebral body below the lower endplate. The engagement mechanism can comprise a plurality of rails along a length of an outer portion of the first sidewall from a proximal end to a distal end and a plurality of grooves along a length of an inner portion of the second sidewall from a proximal end to a distal end for selective engagement with the one or more rails.

In some exemplary embodiments, an intervertebral implant can be provided, comprising a threaded shell configured to be placed within a disc space between vertebral bodies, an expansion mechanism within the threaded shell configured to expand the threaded shell upon actuation, and an actuation mechanism configured to actuate the expansion mechanism.

The threaded shell can comprise an upper endplate, and a lower endplate; wherein the upper endplate and lower endplate separate and expand upon actuation of the actuation mechanism. The intervertebral implant can further comprise one or more graft windows within the threaded shell configured to allow bone growth inducing material to be placed within the threaded shell. The actuation mechanism can comprise a square nut. Rotation of the actuation mechanism in a first direction can expand the threaded shell in an expanded state, and rotation of the actuation mechanism in a second direction can retract the threaded shell to a non-expanded state.

In some exemplary embodiments, a method of providing an intervertebral implant can be provided, comprising drilling a hole within a disc space and a portion of a first vertebral body adjacent to the disc space at a first end and a second vertebral body adjacent to the disc space at a second opposite end, threading an expandable spacer including a threaded shell with an expansion mechanism enclosed within the threaded shell through the hole, and expanding the expandable spacer within the hole once the expandable spacer is in position within the hole.

The method can further comprise actuating an actuation mechanism within the threaded shell to expand the expandable spacer within the hole. The threaded shell can comprise an upper endplate, and a lower endplate, wherein the upper endplate and lower endplate separate and expand upon actuation of the actuation mechanism.

In some embodiments, an intervertebral implant comprises a first endplate having an upper surface and a lower surface, wherein the first endplate comprises a first side wall that extends from the first endplate; and a second endplate having an upper surface and a lower surface, wherein the second endplate includes a second side wall that extends from the second endplate;
wherein the first side wall and the second side wall are configured to engage one another and provide a selective height between the first endplate and the second endplate; wherein the first side wall and the second side wall form a substantially hollow portion substantially enclosed by the first endplate, second endplate, first side wall and the second side wall; and wherein the substantially hollow portion is configured to receive bone growth inducing material.

In some embodiment, an intervertebral implant comprises an upper endplate having a proximal end, a distal end, a first side and an opposing second side; a lower endplate having a proximal end, a distal end, a first side and an opposing second side; a first sidewall extending along a periphery of the first side, distal end and second side of the upper endplate towards the lower endplate; a second sidewall extending along a periphery of the first side, distal end and second side of the lower endplate towards the upper endplate; and an engagement mechanism for selective engagement of the first sidewall with the second sidewall configured to provide a selective distance between the upper endplate and the lower endplate; wherein the upper endplate, lower endplate, first sidewall and second sidewall partially enclose a substantially hollow portion configured to receive bone growth inducing material therein.

These and other objects, features and advantages of the present disclosure will become apparent upon reading the following detailed description of embodiments of the present disclosure, when taken in conjunction with the appended claims. It should be understood that the detailed description and specific examples, while indicating the preferred or exemplary embodiments of the disclosure, are intended for purposes of illustration only and are not intended to limit the scope of the disclosure.

BRIEF DESCRIPTION OF THE DRAWINGS

The foregoing and other exemplary objects of the present disclosure will be apparent upon consideration of the following detailed description, taken in conjunction with the accompanying exemplary drawings and claims, in which like reference characters refer to like parts throughout, and in which:

Figure 1:
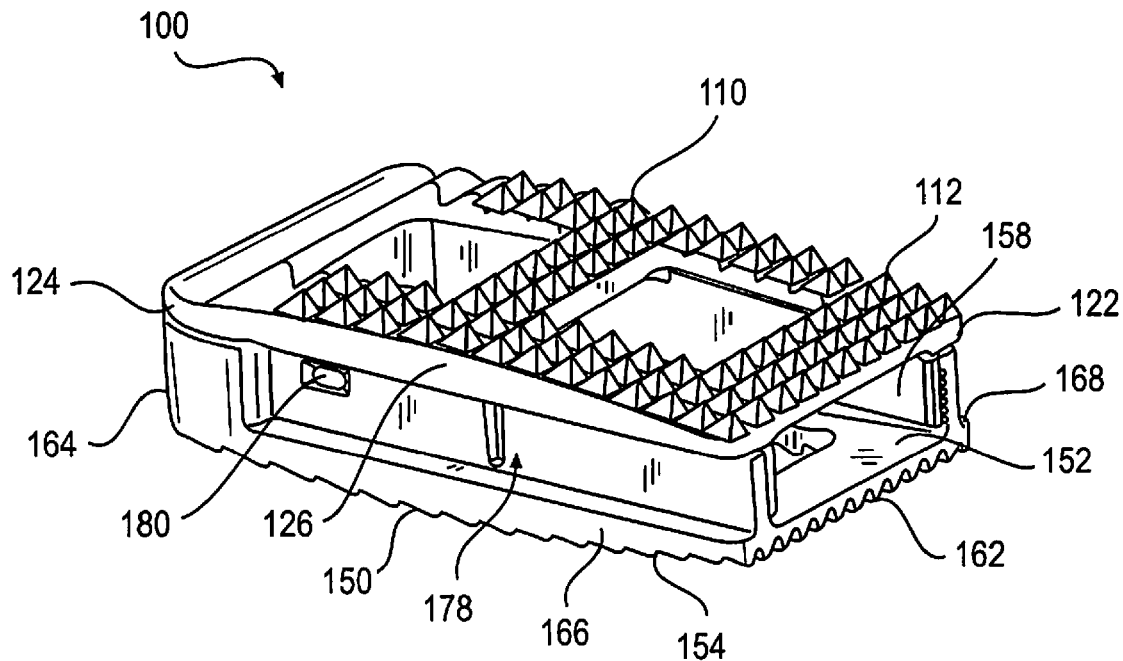
FIG. 1 illustrates a side perspective view of an intervertebral implant according to an exemplary embodiment of the present disclosure.
Figure 2:
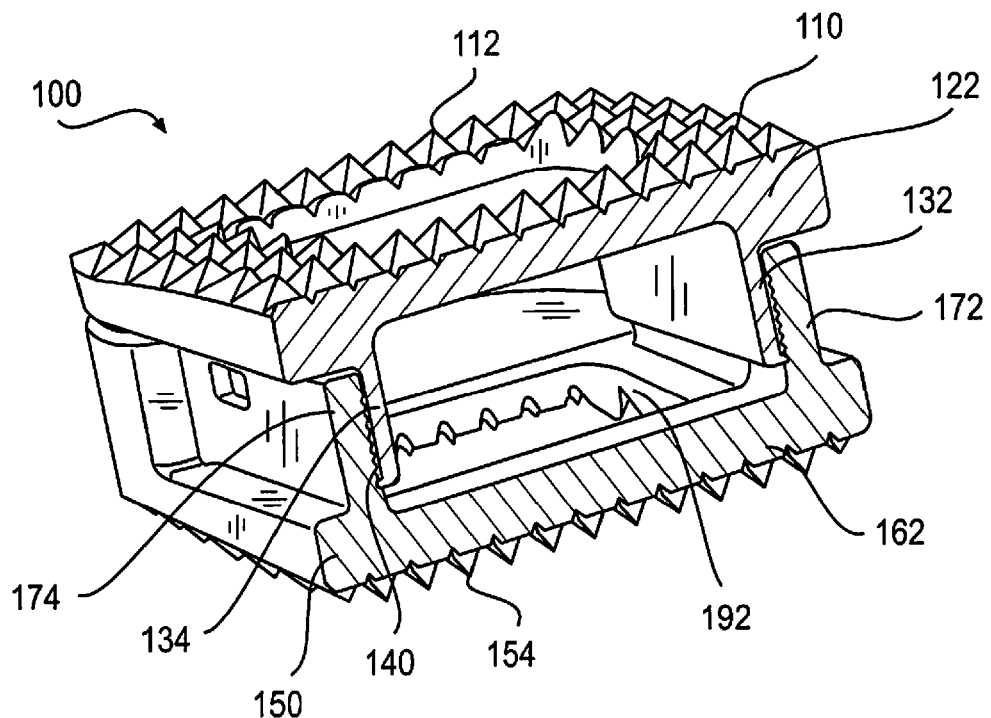
FIG. 2 illustrates a front perspective view of an intervertebral implant according to an exemplary embodiment of the present disclosure.
Figure 3:
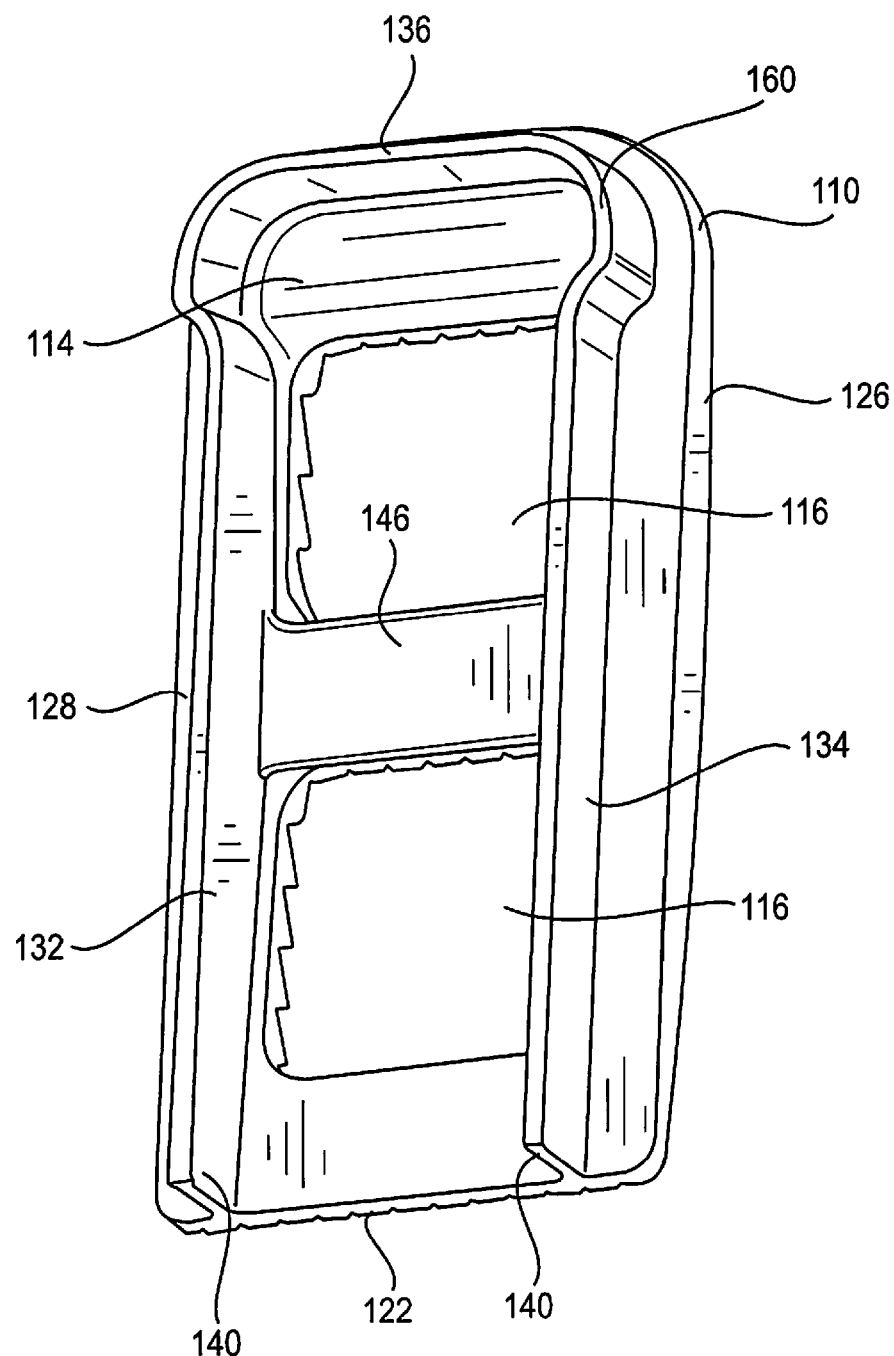
FIG. 3 illustrates a bottom perspective view of an upper endplate of an intervertebral implant according to an exemplary embodiment of the present disclosure.
Figure 4:
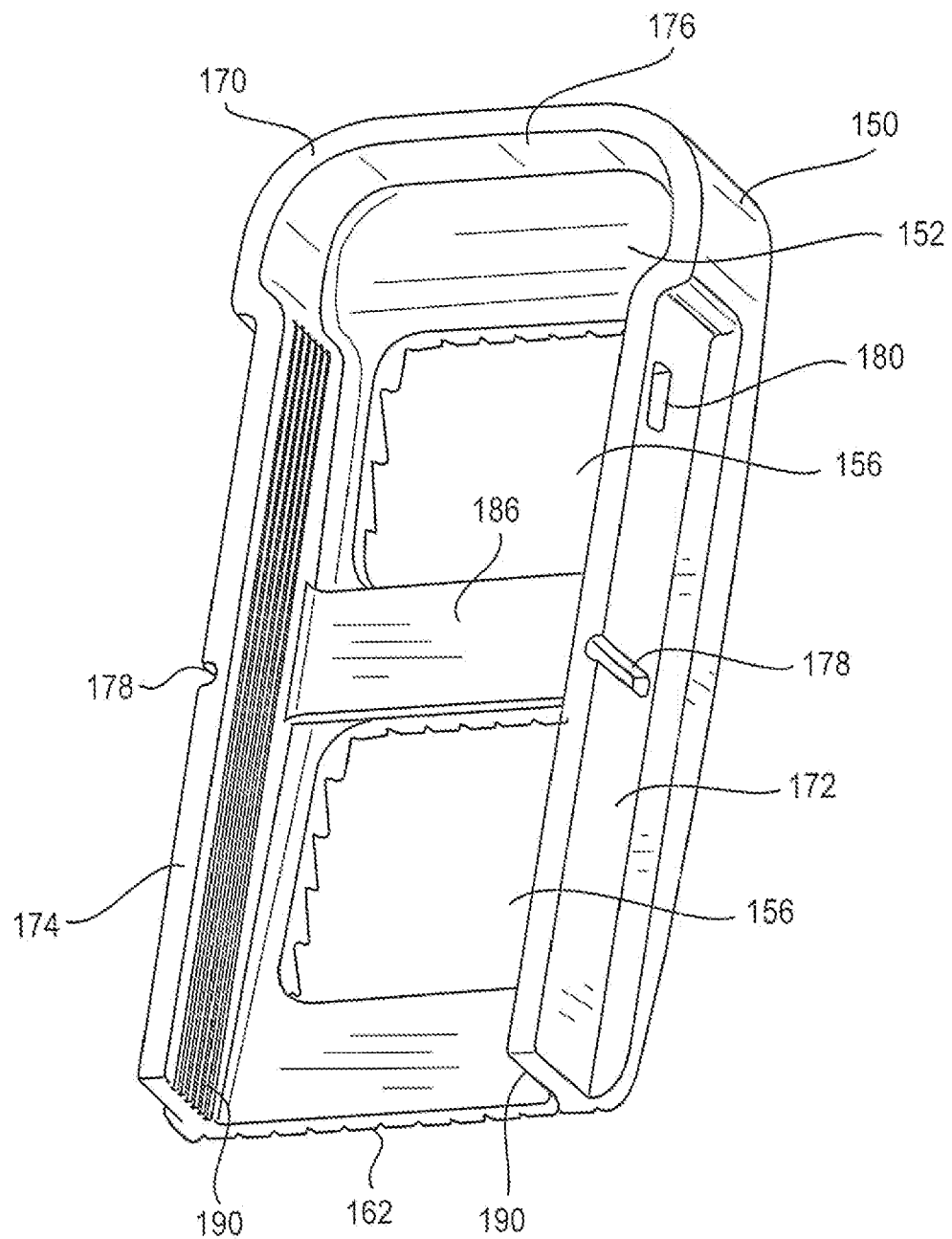
FIG. 4 illustrates a top perspective view of a lower endplate of an intervertebral implant according to an exemplary embodiment of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure.

DETAILED DESCRIPTION OF EXEMPLARY EMBODIMENTS OF DISCLOSURE

Exemplary embodiments of the apparatuses and methods of the present disclosure will now be described with reference to the figures. The following description of the various embodiments is merely exemplary in nature and is in no way intended to limit the scope of the disclosure, its application, or uses.

A spinal fusion is typically employed to eliminate pain caused by the motion of degenerated disk material. Upon successful fusion, a fusion device becomes fixed within the intervertebral disc space. The present disclosure advantageously provides novel fusion devices that can be inserted in a first height and expanded to a second height that is greater than the first height. Advantageously, the fusion devices include novel expansion mechanisms that can expand the devices in a steady and controlled manner.

Referring to FIGS. 1-4, in some embodiments, an intervertebral implant 100 is provided comprising an upper endplate 110 and a lower endplate 150. The upper endplate 110 and lower endplate 150 can be manufactured from a number of materials including titanium, stainless steel, titanium alloys, non-titanium metallic alloys, polymeric materials, plastics, plastic composites, PEEK, PEEK with a titanium spray, ceramic, and elastic materials. In some embodiments, nitinol can be used as a material. In some embodiments, an HA coating can be applied to the endplates. In some embodiments, the intervertebral implant 100 can be configured to be placed down an endoscopic tube and into the disc space between adjacent vertebral bodies.

In some embodiments, the upper endplate 110 can have a proximal end 122, a distal end 124, a first side 126, a second side 128 opposite to the first side 126, an upper surface 112 and a lower surface 114. The lower endplate 150 can have a proximal end 162, a distal end 164, a first side 166, a second side 168 opposite to the first side 166, an upper surface 152 and a lower surface 154. The upper surface 112 of the upper endplate 110 and the lower surface 154 of the lower endplate 150 can include texturing to aid in gripping the adjacent vertebral bodies. Although not limited to the following, the texturing can include teeth, ridges, friction increasing elements, keels, or gripping or purchasing projections.

Figure 35:
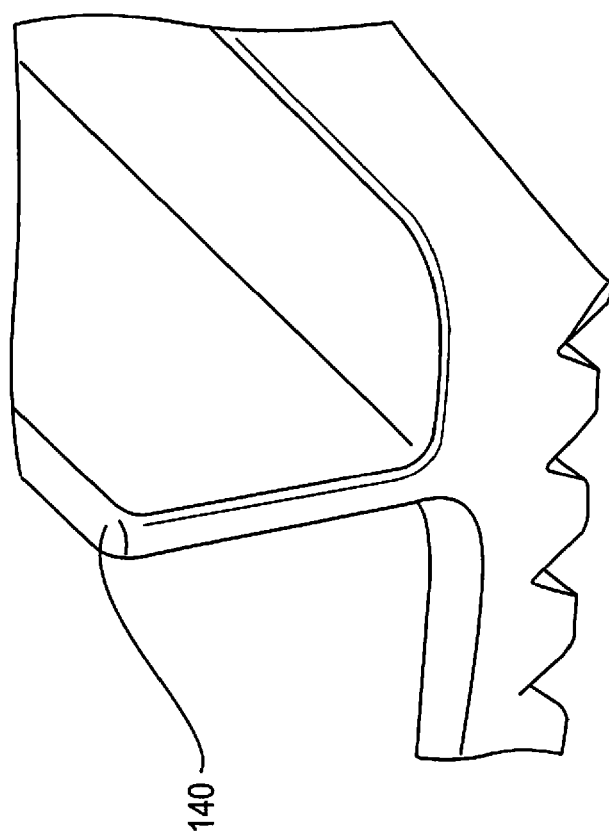
FIG. 35 shows a close up view of a rail.

In some embodiments, the upper endplate 110 can have one or more slots 116 configured to allow fusion of bone growth inducing material within the intervertebral implant 100 and an adjacent vertebral body. In some embodiments, the upper endplate 110 can have two slots 116 on opposite sides of a middle portion 146 of the upper endplate 110. The upper endplate 110 can have a sidewall 160 extending from the lower surface 114 having a first side portion 134 at a first side 126 of the upper endplate 110, a second side portion 132 at a second side 128 of the upper endplate 110, and a distal portion 136 at a distal end 124 of the upper endplate 110. Although the sidewall 160 is shown as integral with the upper endplate 110, the sidewall 160 can be separate from the upper endplate 110 in some embodiments, and can be releasably engaged with the upper endplate 110 in some embodiments. The sidewall 160 can extend along an inner periphery of the first side 126, distal end 124 and the second side 128 of the upper endplate 110. In other embodiments, the upper endplate 110 can comprise a pair of sidewalls independent from one another, such that a first sidewall extends along a first side 126 of the upper endplate 110 and a second sidewall extends along a second side 128 of the upper endplate. In some embodiments, the sidewall 160 can have one or more rails 140 (shown in FIG. 35) provided along a length of the sidewall 160 and parallel to the upper endplate 110. The rails 140 can be provided along a length of the first side portion 134 and the second side portion 132 of the sidewall 160. In some embodiments, the one or more rails 140 are aligned vertically, one on top of the other.

Figure 36:
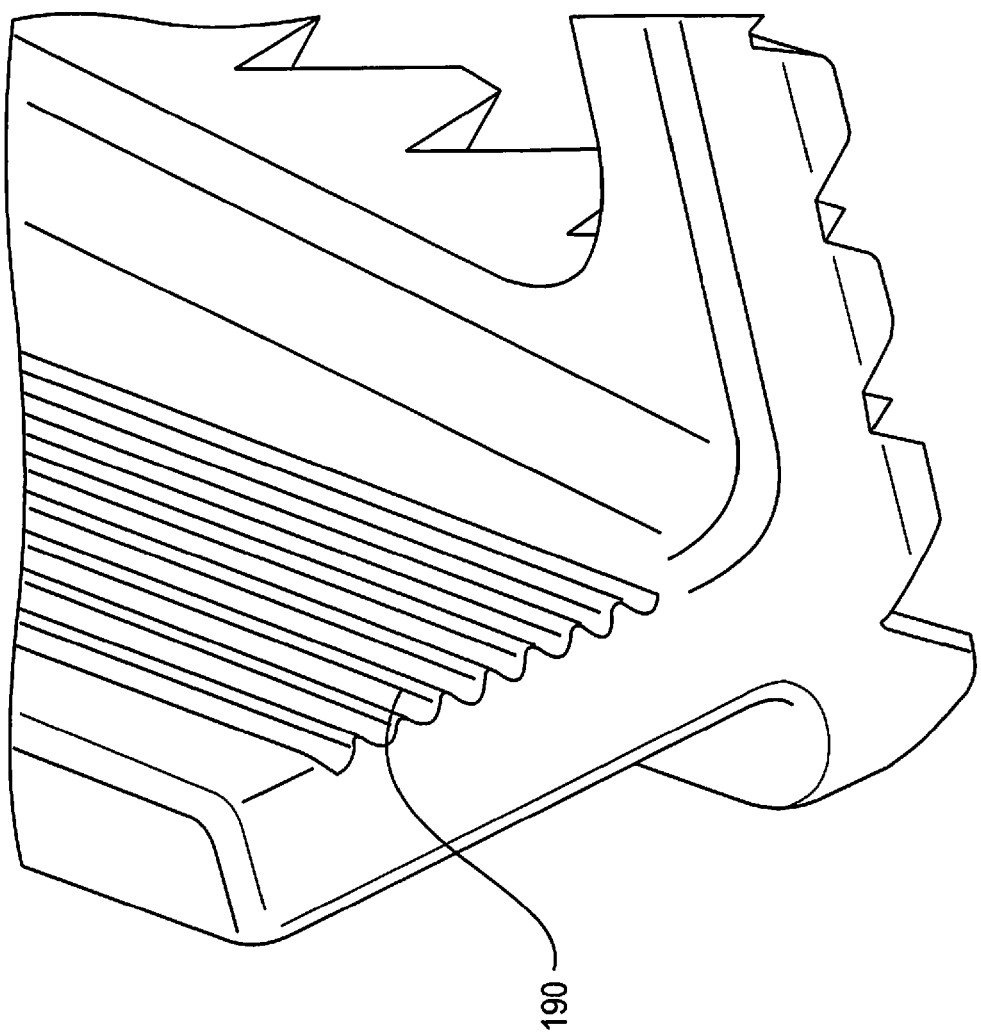
FIG. 36 shows a close up view of grooves.

In some embodiments, the lower endplate 150 can have one or more slots 156 configured to allow fusion of bone growth inducing material within the intervertebral implant 100 and an adjacent vertebral body. In some embodiments, the lower endplate 150 can have two slots 156 on opposite sides of a middle portion 186 of the lower endplate 150. The lower endplate 150 can have a sidewall 170 extending from the upper surface 152 having a first side portion 174 at a first side 166 of the lower endplate 150, a second side portion 172 at a second side 168 of the lower endplate 150, and a distal portion 176 at a distal end 164 of the lower endplate 150. Although the sidewall 170 is shown as integral with the lower endplate 150, the sidewall 170 can be separate from the lower endplate 150 in some embodiments, and can be releasably engaged with the lower endplate 150 in some embodiments. The sidewall 170 can extend along an inner periphery of the first side 166, distal end 164 and the second side 168 of the lower endplate 150. In other embodiments, the lower endplate 150 can comprise a pair of sidewalls independent from one another, such that a first sidewall extends along a first side 166 of the lower endplate 110 and a second sidewall extends along a second side 168 of the lower endplate. In some embodiments, the sidewall 170 can have one or more grooves 190 (shown in FIG. 36) provided along a length of the sidewall 170 and parallel to the lower endplate 150. The grooves 190 can be provided along a length of the first side portion 174 and the second side portion 172 of the sidewall 170. In some embodiments, the one or more grooves 190 are aligned vertically, one on top of the other.

Figure 5:
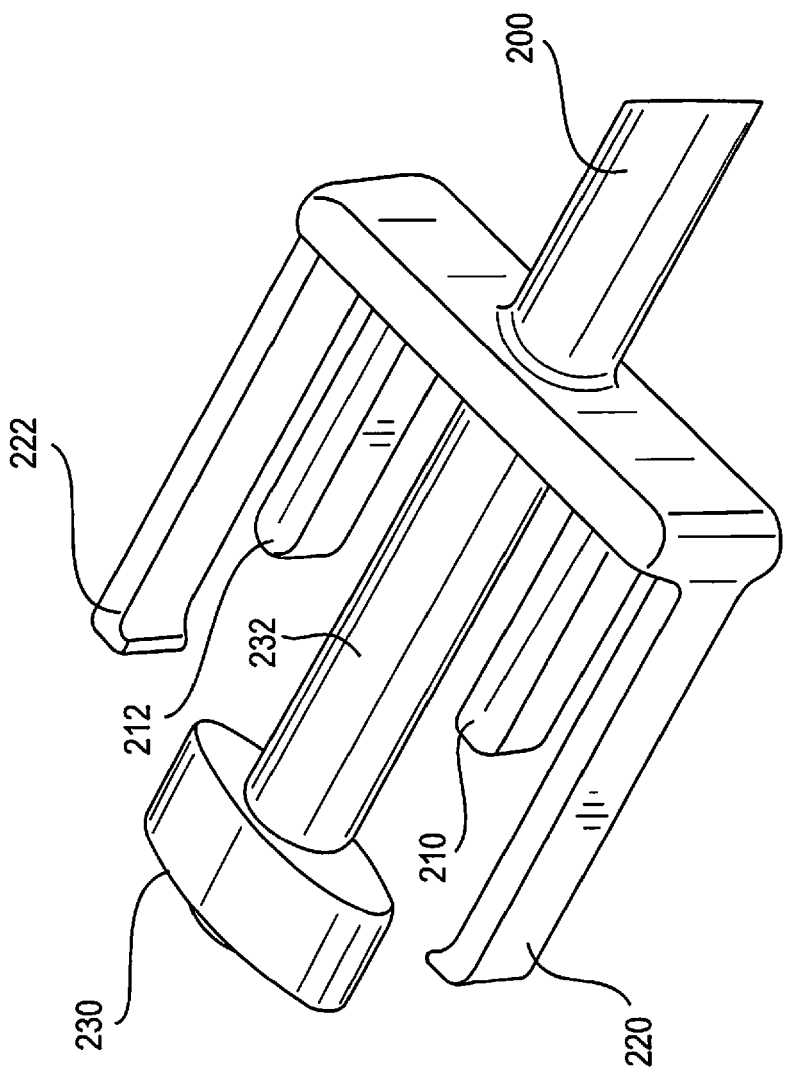
FIG. 5 illustrates a top perspective view of an implant holder with a cam shaft according to an exemplary embodiment of the present disclosure.
Figure 6:
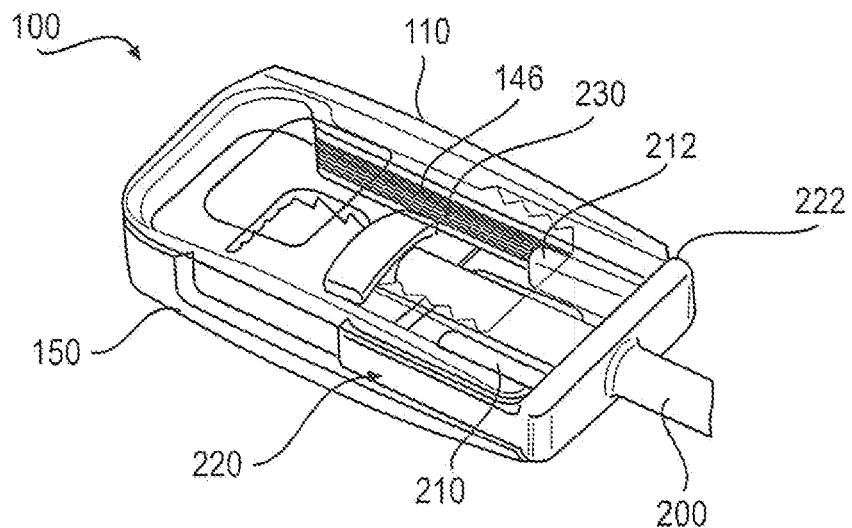
FIG. 6 illustrates a side perspective view of an implant holder secured to an intervertebral implant according to an exemplary embodiment of the present disclosure.
Figure 7:
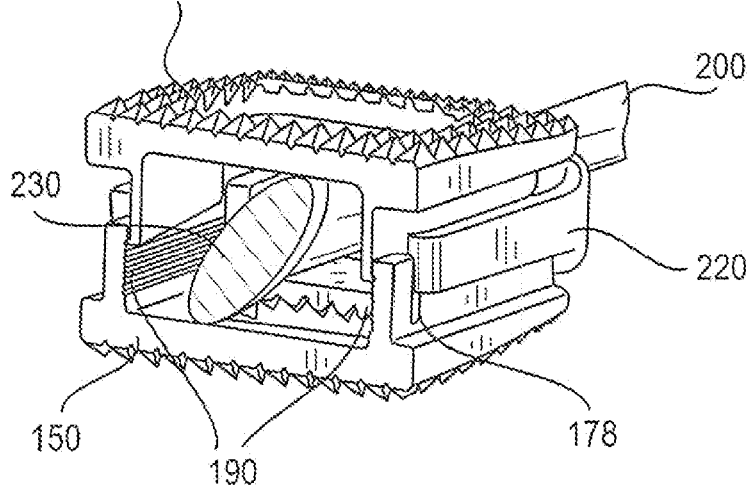
FIG. 7 illustrates a cross-section of a front perspective view of a cam within an intervertebral implant according to an exemplary embodiment of the present disclosure.
Figure 8:
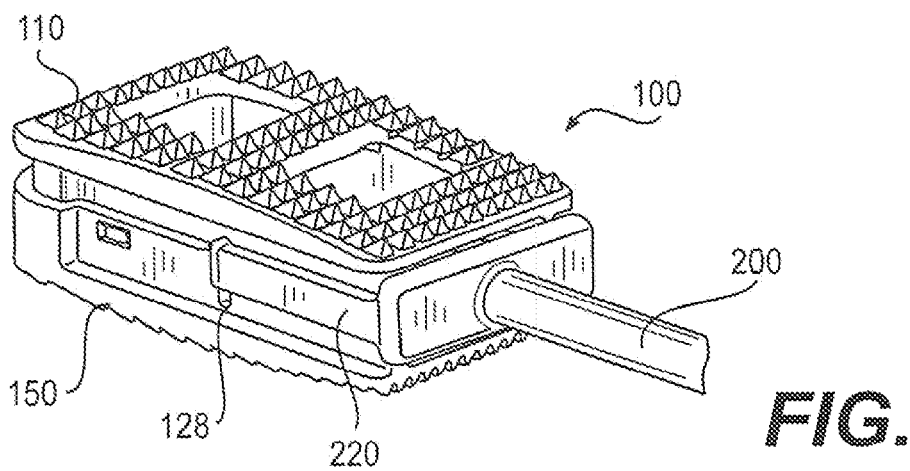
FIG. 8 illustrates a side perspective view of an implant holder secured to an intervertebral implant according to an exemplary embodiment of the present disclosure.

In some embodiments, the rails 140 of the sidewall 160 can correspond to the grooves of the sidewall 170, allowing engagement of the sidewall 160 of the upper endplate 110 with the sidewall 170 of the lower endplate 150. In some embodiments, the rails 140 and grooves 190 can be provided along one millimeter intervals, and can range from 0.2 millimeter intervals to 6 millimeter intervals. In other embodiments, the rails 140 and grooves 190 can be provided at less than one millimeter intervals, or greater than one millimeter intervals. This can provide for selective engagement of the rails 140 with the grooves 190, which can provide for variable heights between the upper endplate 110 and the lower endplate 150. This can provide for expansion of the intervertebral implant 100 (e.g., via an instrument as shown in FIG. 5) as may be necessary, as will be described below. In some embodiments, a substantially hollow portion 192 is provided between the engaged sidewalls 160, 170. The hollow portion can be used to pack bone graft or similar bone growth inducing material within the intervertebral implant 100. This can advantageously provide for stronger fusion of the intervertebral implant 100 with adjacent vertebral bodies. The sidewalls can provide for complete enclosure along the side portions of the endplates and the distal ends of the endplates, and provide an opening 158 between the proximal ends of the endplates. For example, the sidewalls 160 and 170 can provide for complete enclosure between the first side 126 of the upper endplate 110 and the first side 166 of the lower endplate 150, the second side 128 of the upper endplate 110 and the second side 168 of the lower endplate 150, and the distal end 124 of the upper endplate 110 and the distal end 164 of the lower endplate 150. An opening 158 can be provided between the proximal end 122 of the upper endplate 110 and the proximal end 162 of the lower endplate 150.

In some embodiments, the upper endplate 110 can have grooves and the lower endplate 150 can have rails. Other engagement mechanisms can also be used, such as a pin within a slot, clips, fasteners, other mechanical mechanisms, magnets, or any other attachment mechanisms and the present disclosure is not limited to any particular type of engagement mechanism between the upper and lower endplates.

In some embodiments, the sidewall 170 can have an implant holder interface 178 for engagement with an implant holder, as will be discussed below. The implant holder interface 178 can be but is not limited to a groove, hole, ridge or other engagement mechanism. The implant holder interface 178 can be provided along the first side portion 174 and the second side portion 172 of the sidewall 170. The sidewall 170 can have an end cap interface 180 for engagement with an end cap, as will be discussed below. The end cap interface 180 can be but is not limited to a groove, hole, ridge or other engagement mechanism. The end cap interface 180 can be provided along the first side portion 174 and the second side portion 172 of the sidewall 170.

Referring to FIGS. 5-8, in some embodiments, an implant holder 200 is provided that can be used to deliver the intervertebral implant 100 and raise the upper endplate 110 with respect to the lower endplate 150. In some embodiments, the implant holder 200 can have inner implant interfacing tangs 210 and 212, outer implant interfacing tangs 220 and 222, and cam shaft 230, which can be placed in the center of the interfacing tangs. Outer implant interfacing tangs 220 and 222 can be longer than the inner interfacing tangs 210 and 212. Cam shaft 230 can be connected to a middle tang 232.

In some embodiments, the implant holder 200 can be inserted within the opening 158 between the proximal end 122 of the upper endplate 110 and the proximal end 162 of the lower endplate 150, such that outer implant interfacing tangs 220 and 222 are placed outside of the first side portion 174 and second side portion 172 of the lower endplate 150, respectively. The inner implant interfacing tangs 210 and 212 can be placed inside of the first side portion 134 and the second side portion 132 of the upper endplate 110. The cam 230 can be placed underneath a middle portion 146 of the upper endplate 110 and middle portion 186 of the lower endplate 150.

In some embodiments, as the cam 230 is turned, it presses against the middle portion 146 of the upper endplate 110 and middle portion 186 of the lower endplate 150, raising the upper endplate 110 with respect to the lower endplate 150. As the upper endplate 110 rises, the engagement rails 140 snap out of their respective grooves 190 and snap back in to the next corresponding grooves 190. When the desired height of the upper endplate 110 with respect to the lower endplate 150 is achieved, the cam 230 can be turned back and the implant holder 200 can be removed from the intervertebral implant 100. In some exemplary embodiments, the cam 230 can be built inside the intervertebral implant 100, and the implant holder 200 can have an instrument to engage the cam 230 and turn the cam 230.

Figure 9:
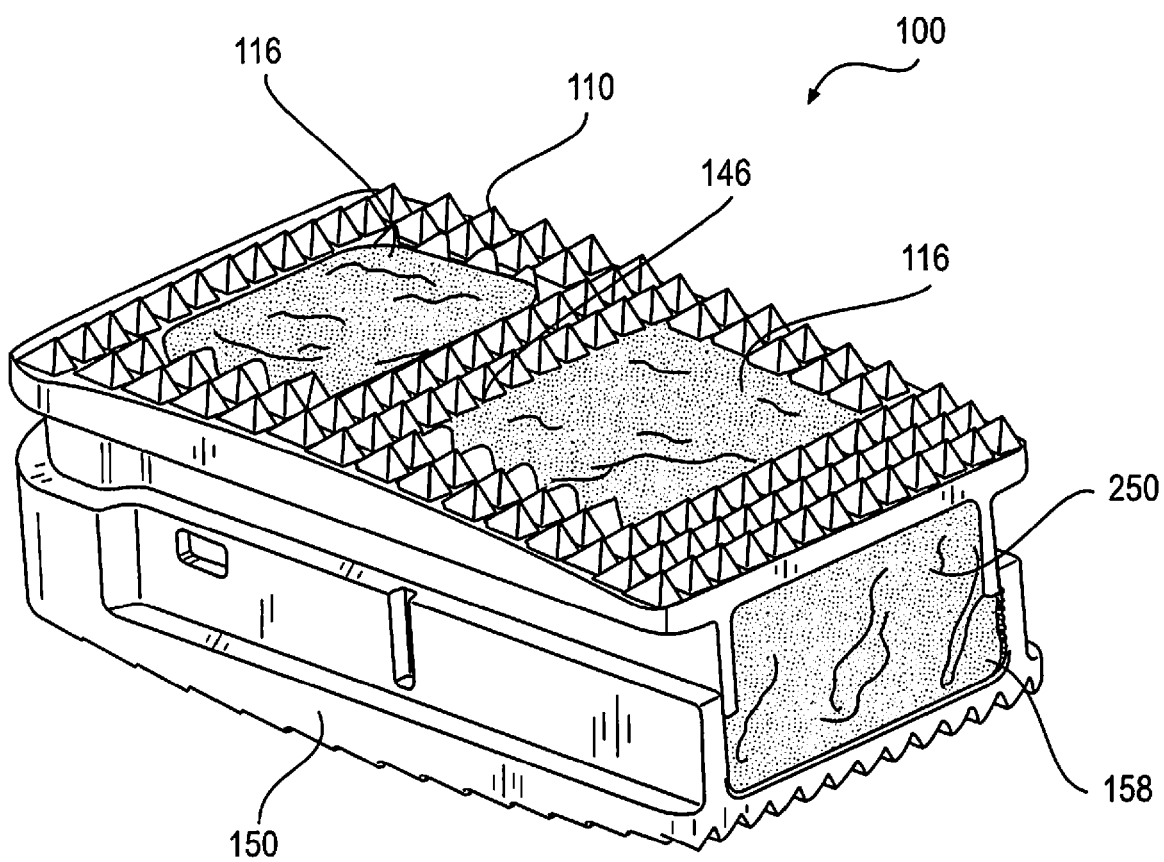
FIG. 9 illustrates a side perspective view of an intervertebral implant filled with bone growth inducing material according to an exemplary embodiment of the present disclosure.

Referring to FIG. 9, in some embodiments, after the intervertebral implant 100 has been expanded, bone graft or similar bone growth inducing material 250 can be placed within the intervertebral implant 100 through, e.g., opening 158 between the upper endplate 110 and the lower endplate 150. In some exemplary embodiments, bone graft or similar bone growth inducing material 250 can be introduced around and within the intervertebral implant 100 to further promote and facilitate the intervertebral fusion. The intervertebral implant 100, in some embodiments, can be packed with bone graft or similar bone growth inducing material to promote the growth of bone through and around the intervertebral implant 100. Some amount of bone graft may also be packed between the endplates of the adjacent vertebral bodies prior to, subsequent to, or during implantation of the fusion device. Some bone graft may also be packed within the intervertebral implant 100 before insertion into the disc space between the vertebral bodies. Slots 116 and 156 can help promote fusion by allowing the bone growth inducing material 250 to exude out of the respective slots and engage with the vertebral bodies engaged with upper endplate 110 and lower endplate 150.

Figure 10:
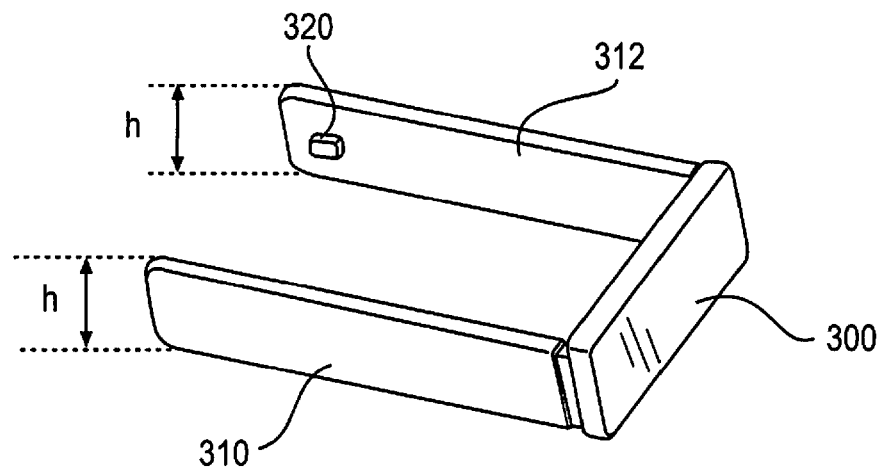
FIG. 10 illustrates a side perspective view of an end cap according to an exemplary embodiment of the present disclosure.
Figure 11:
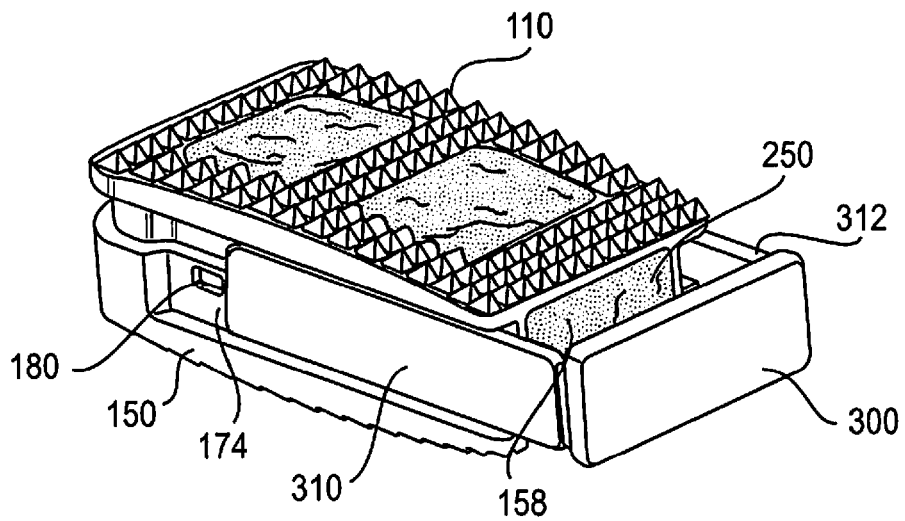
FIG. 11 illustrates a side perspective view of an end cap engaged with an intervertebral implant according to an exemplary embodiment of the present disclosure.
Figure 12:
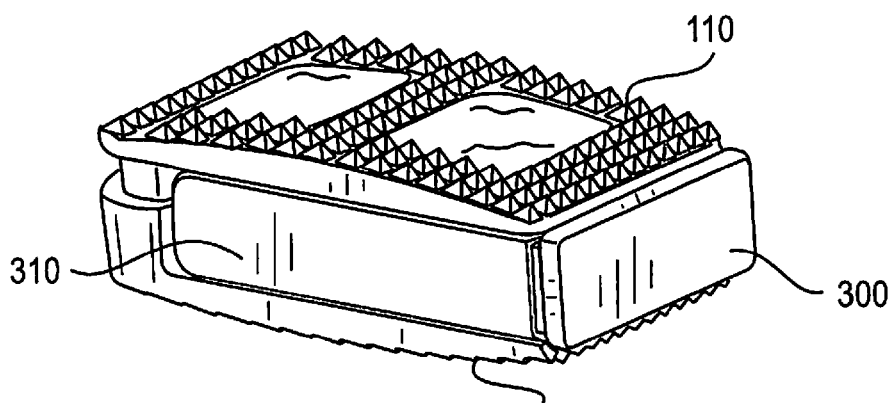
FIG. 12 illustrates a side perspective view of an end cap secured to an intervertebral implant according to an exemplary embodiment of the present disclosure.
Figure 13:
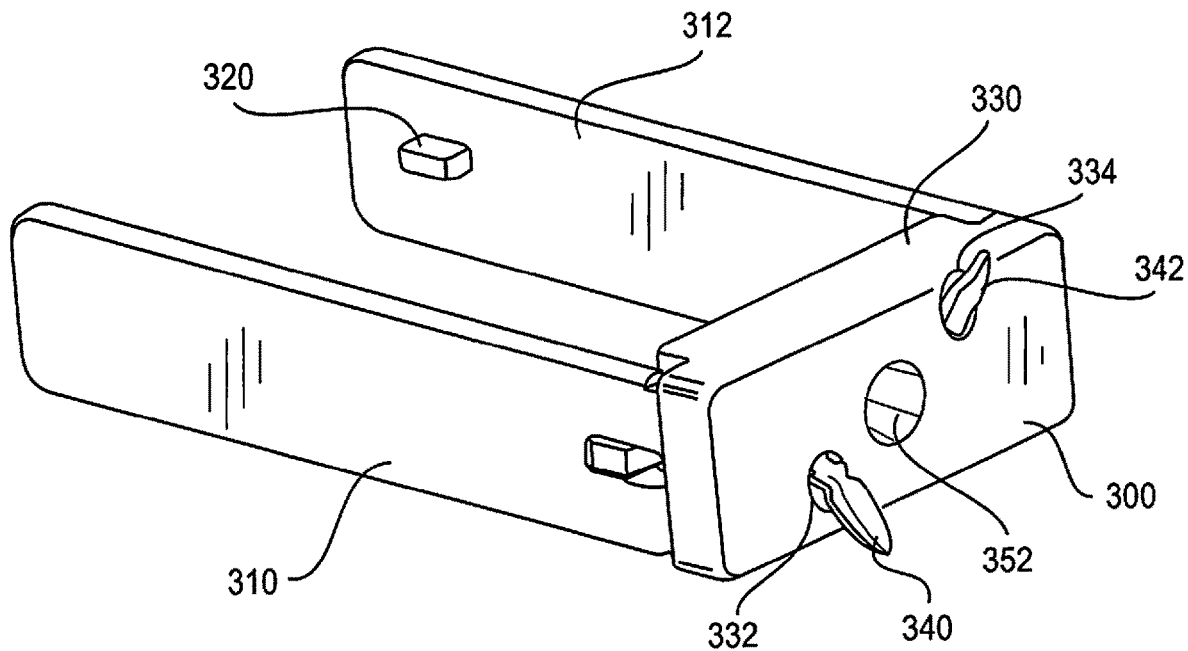
FIG. 13 illustrates a side perspective view of an end cap with spikes according to an exemplary embodiment of the present disclosure.
Figure 14:
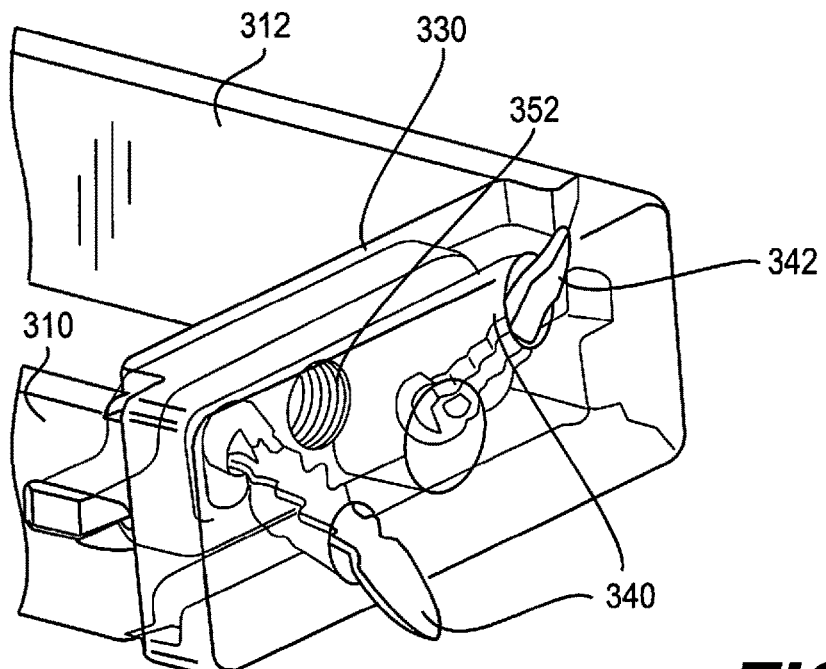
FIG. 14 illustrates a cross-section of a side perspective view of a drive plate of an end cap according to an exemplary embodiment of the present disclosure.
Figure 15:
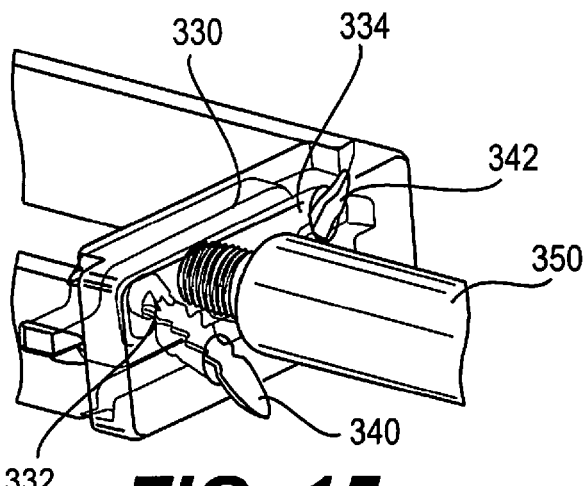
FIG. 15 illustrates a side perspective view of a driver within a drive plate of an end cap according to an exemplary embodiment of the present disclosure.
Figure 16:
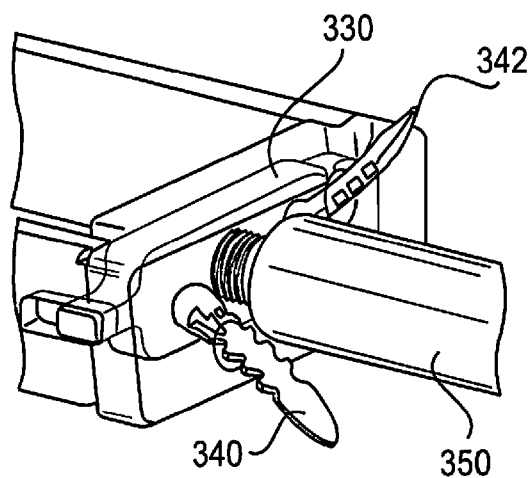
FIG. 16 illustrates a side perspective view of a driver turning within a drive plate of an end cap according to an exemplary embodiment of the present disclosure.
Figure 17:
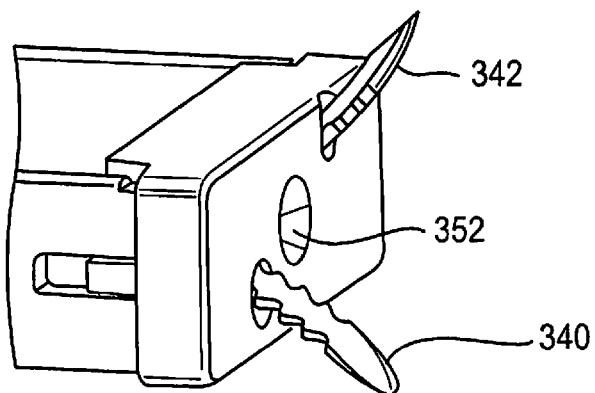
FIG. 17 illustrates a side perspective view of an end cap with spikes according to an exemplary embodiment of the present disclosure.
Figure 18:
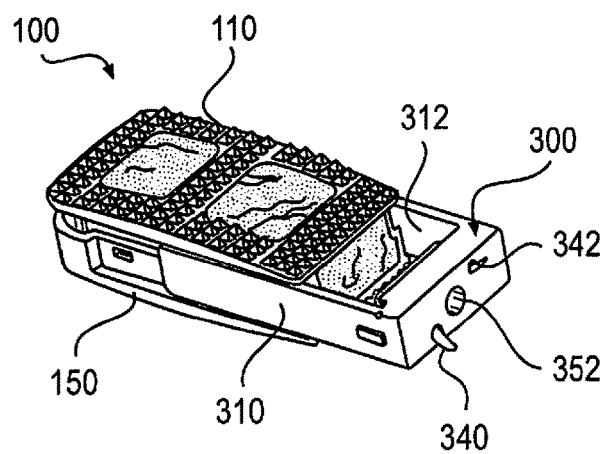
FIG. 18 illustrates a side perspective view of an end cap with a drive plate engaged to an intervertebral implant according to an exemplary embodiment of the present disclosure.
Figure 19:
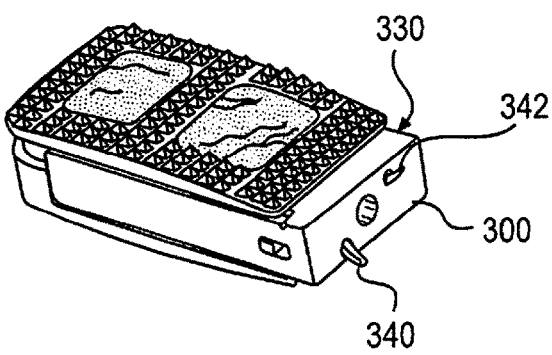
FIG. 19 illustrates a side perspective view of an end cap with a drive plate secured to an intervertebral implant according to an exemplary embodiment of the present disclosure.
Figure 20:
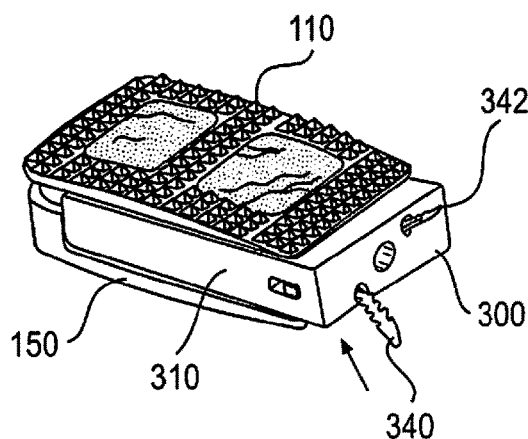
FIG. 20 illustrates a side perspective view of an end cap with spikes engaged to an intervertebral implant according to an exemplary embodiment of the present disclosure.
Figure 21:
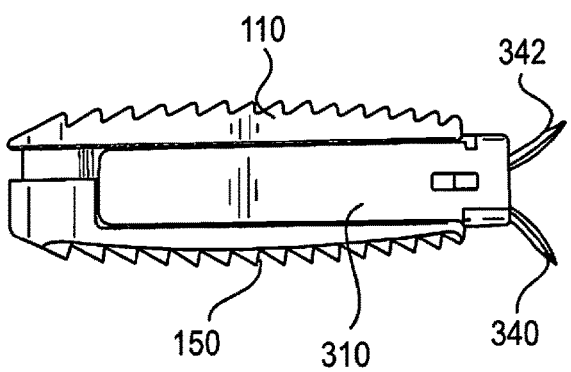
FIG. 21 illustrates a side view of an end cap with spikes secured to an intervertebral implant according to an exemplary embodiment of the present disclosure.
Figure 22:
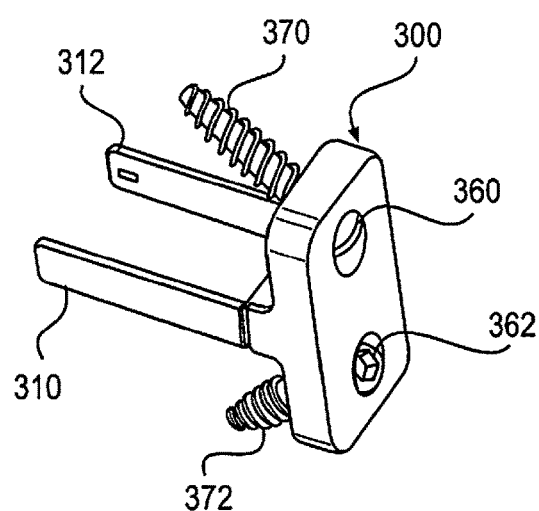
FIG. 22 illustrates a side perspective side view of an end cap with screws according to an exemplary embodiment of the present disclosure.
Figure 23:
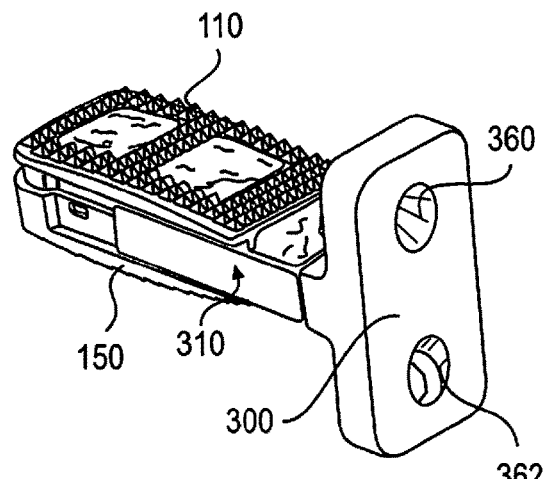
FIG. 23 illustrates a side perspective view of an end cap engaged to an intervertebral implant according to an exemplary embodiment of the present disclosure.
Figure 24:
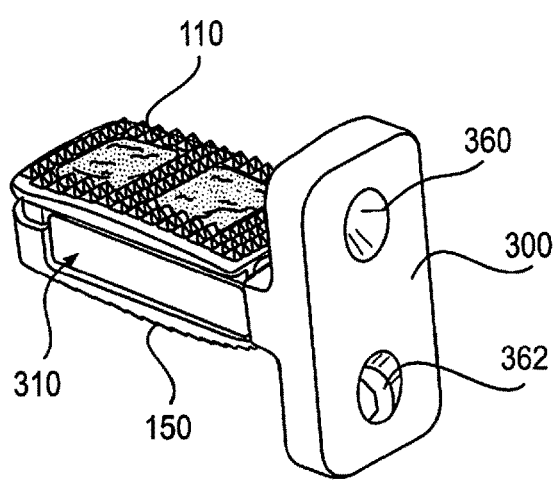
FIG. 24 illustrates a side perspective view of an end cap secured to an intervertebral implant according to an exemplary embodiment of the present disclosure.
Figure 25:
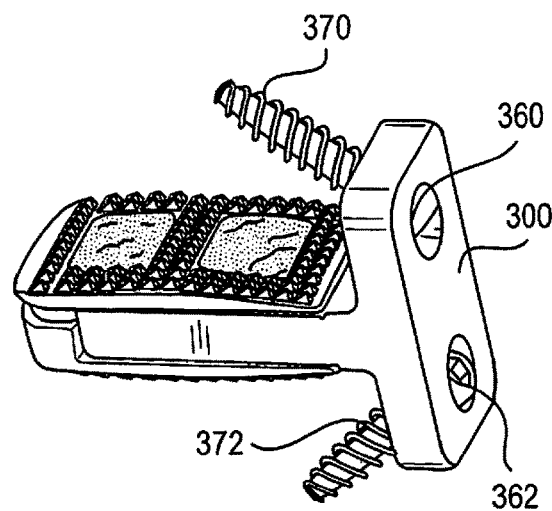
FIG. 25 illustrates a side perspective view of an end cap with screws secured to an intervertebral implant according to an exemplary embodiment of the present disclosure.
Figure 28:
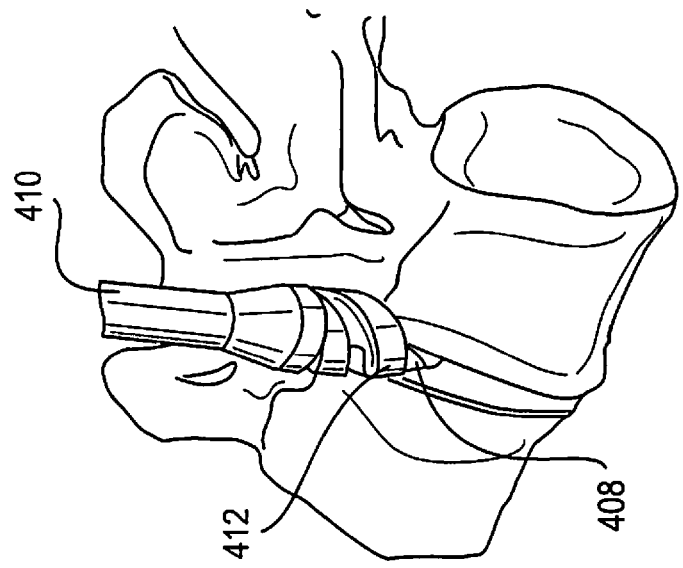
FIG. 28 illustrates a perspective view of a drill within an endoscopic tube according to an exemplary embodiment of the present disclosure.
Figure 27:
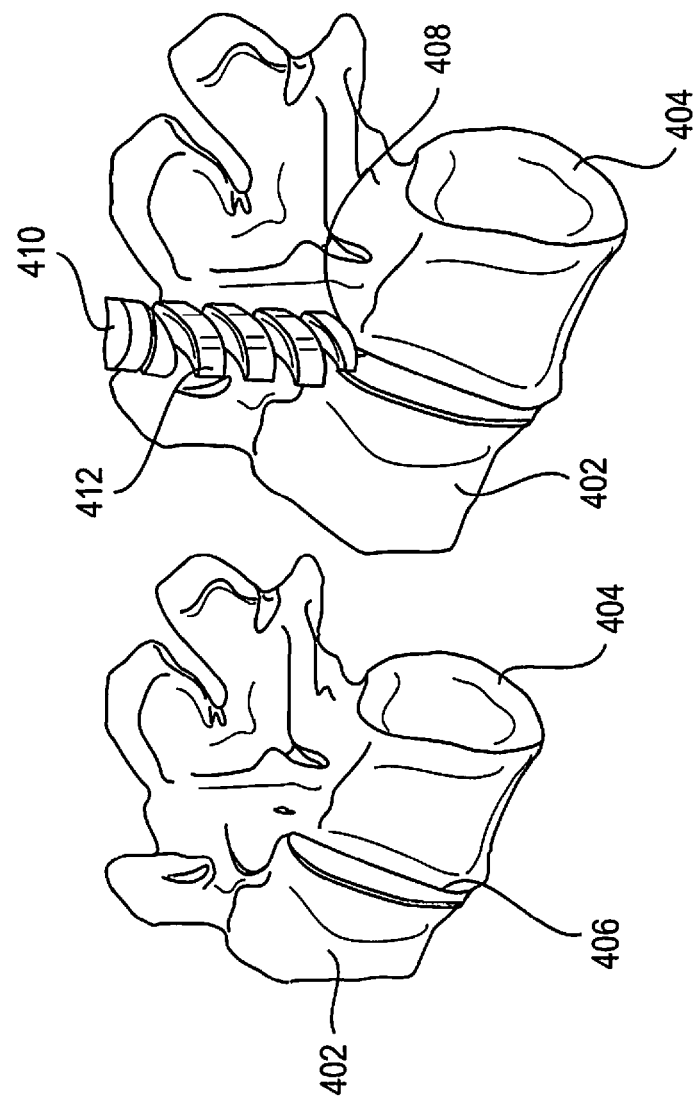
FIG. 27 illustrates a perspective view of a drill within a disc space between two vertebral bodies according to an exemplary embodiment of the present disclosure.
Figure 26:
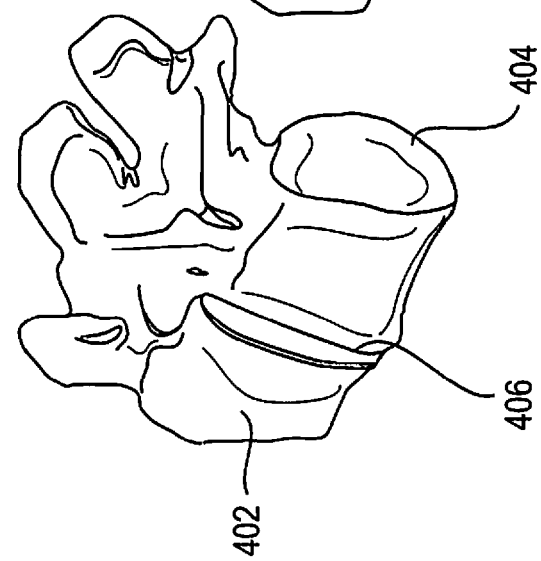
FIG. 26 illustrates a perspective view of a disc space between two vertebral bodies according to an exemplary embodiment of the present disclosure.
Figure 30:
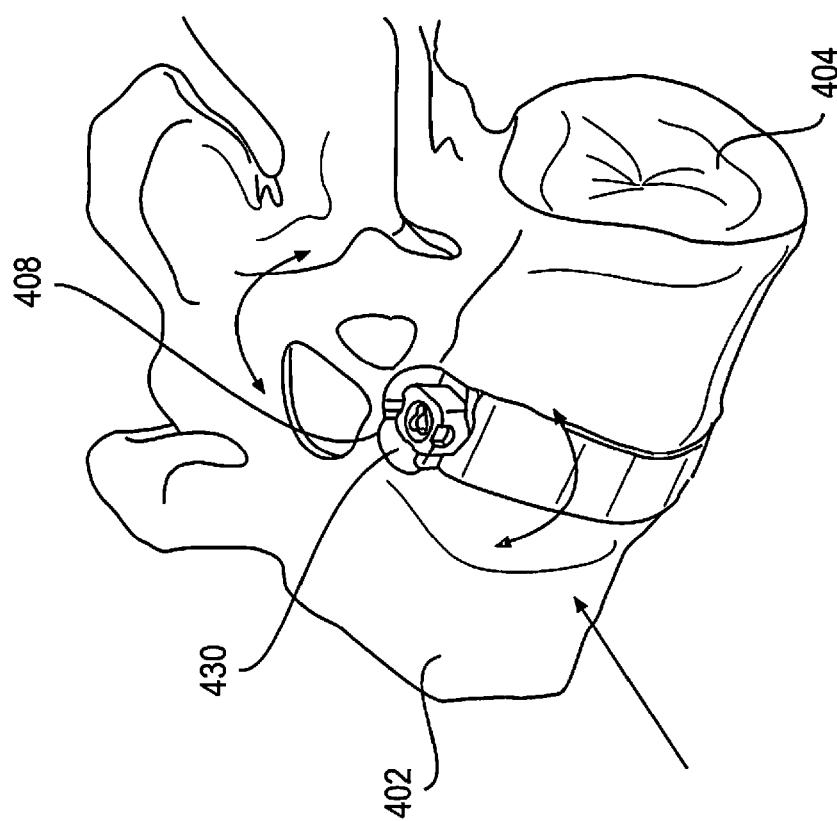
FIG. 30 illustrates a perspective view of an expandable spacer within a drill hole between two vertebral bodies according to an exemplary embodiment of the present disclosure.
Figure 29:
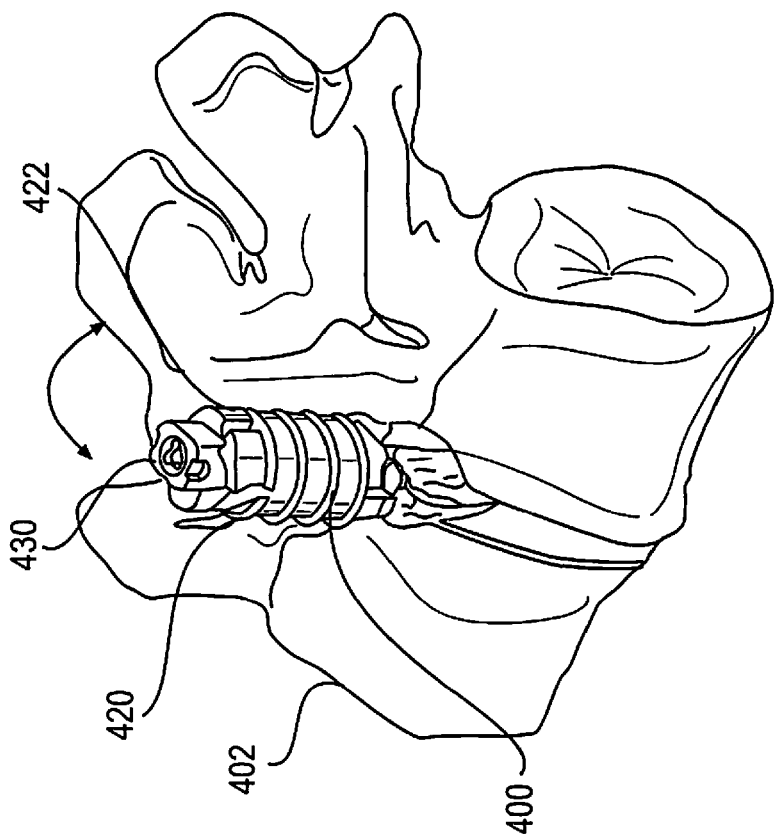
FIG. 29 illustrates a perspective view of an expandable spacer being threaded in a drill hole between two vertebral bodies according to an exemplary embodiment of the present disclosure.

Referring to FIGS. 10-12, in some embodiments, an end cap 300 can be provided having rails 310 and 312. The end cap 300 can be made of the same material as the upper endplate 110 and lower endplate 150. The end cap 300 can have a locking interface 320 on the rail 310 to engage with the end cap interface 180 of the first side portion 174 of sidewall 170, and a locking interface 320 on the rail 312 to engage with the end cap interface 180 of the second side portion 172 of the sidewall 170. Once the locking interfaces 320 are secured in place with the end cap interfaces 180, the end cap 300 can seal the opening 158 between the upper endplate 110 and the lower endplate 150. The end cap 300 can be selected so that the height h of the rails 310 and 312 correspond to the height between the upper endplate 110 and the lower endplate 150. The rails 310 and 312 can engage a lower surface of the upper endplate 110 and an upper surface of the lower endplate 150, providing extra support between the upper endplate 110 and the lower endplate 150, and helping maintain the height between the upper endplate 110 and the lower endplate 150.

In some exemplary embodiments, the height h of the rails 310 and 312 can be slightly greater than the distance between the upper endplate 110 and the lower endplate 150, and can provide extra support and help raise the upper endplate 110 with respect to the lower endplate 150 even farther. For example, the distance between the upper endplate 110 and the lower endplate 150 can be four millimeters, and an end cap with a height h of five millimeters of the rail 310 can be used to raise the upper endplate 110 with respect to the lower endplate 150.

Referring to FIGS. 13-17, in some exemplary embodiments, a drive plate 330 can be provided on the end cap 300. The drive plate 330 can have one or more openings, such as opening 332 and opening 342, and one or more spikes, such as spike 340 and spike 342. The spikes 340 and 342 can be made of the same material as the upper endplate 110 and lower endplate 150. In some embodiments, the spikes 340 and 342 can have ridges and grooves that extend along or from an elongated body. In addition, in some embodiments, the spikes 340 and 342 can comprise a spherical head. Advantageously, the spikes 340 and 342 can be inserted into a vertebral body to help secure the vertebral implant 100 to the vertebral bodies. The opening 332 can be provided closer to the lower endplate 150 and the opening 334 can be provided closer to the upper endplate 110. The drive plate 330 can have a thread hole 352 at a proximal portion of the drive plate 330. A driver 350 can be used and threaded into the thread hole 352. When the driver is turned in a first direction (e.g., counterclockwise), the distal portion of the drive plate 330 is pushed away from the proximal portion of the drive plate 330, and the spikes 340 and 342 are advanced out of the openings 332 and 334, respectively. Turning the driver 350 in a second direction (e.g., clockwise) can retract the spikes 340 and 342 back into the openings 332 and 334.

Referring to FIGS. 18-21, in some exemplary embodiments, the end cap 300 can engage with a vertebral implant 100 as discussed above. Once the end cap 300 is secured and the vertebral implant 100 is in place, a driver 350 can be inserted into the thread hole 352 and turned to advance the spikes 340 and 342. The spike 340 can be advanced in a first direction and driven into a vertebral body below the lower endplate 150, and the spike 342 can be advanced in a second direction and driven into a vertebral body above the upper endplate 110. This can help secure the vertebral implant 100 to the vertebral bodies so that posterior fixation or other procedures are not necessary to secure the vertebral implant 100 to the vertebral bodies.

Referring to FIGS. 22-25, in some exemplary embodiments, an end cap 300 can be provided with openings 30 and 362 with screws 370 and 372, respectively. Once the end cap 300 is secured and the vertebral implant 100 is in place, the screw 370 can be advanced in a first direction through opening 360 and driven into a vertebral body above the upper endplate 110, and the screw 372 can be advanced in a second direction and driven into a vertebral body below the lower endplate 150. This can help secure the vertebral implant 100 to the vertebral bodies so that posterior fixation or other procedures are not necessary to secure the vertebral implant 100 to the vertebral bodies.

In additional embodiments, a threaded expandable spacer can be provided that can expand in-situ. By providing a threaded expandable spacer 400, this helps to decrease migration and subsidence. Furthermore, the threaded expandable spacer advantageously provides maximum amount of contact surface area, thereby increasing purchase into adjacent vertebral bodies. Furthermore, the threaded expandable spacer can work on its own, such that supplemental fixation (e.g., posterior fixation) may not be necessary and can be optional.

Referring to FIGS. 26-30, a disc space 406 is shown between vertebral body 402 and vertebral body 404. A drill 412 can be inserted through an endoscopic tube 410 to drill a hole 408 within the disc space 406, and within the vertebral bodies 402 and 404. That is, the drill diameter is a little larger than the height of the disc space 406 such that a portion of the vertebral bodies 402 and 404 is also drilled. Once the hole 408 is drilled, an endoscopic tube 410 can be used to deliver a threaded expandable spacer 400 into the drill hole 408. The threaded expandable spacer 400 can have a shell 435 and threads 420 on the shell 435, and a nut 430 or other mechanism for engagement on a proximal end 422 of the threaded expandable spacer 400. An actuation mechanism can be used to engage the nut 430 so that it can be turned to turn the threaded expandable spacer 400 and drive the threads 420 of the threaded expandable spacer 400 into the drill hole 408. In some embodiments, the diameter of the drill 412 can be slightly less than the diameter of the threaded expandable spacer 400, so that the threaded expandable spacer 400 is fit tightly into the drill hole 408 as it is threaded into the drill hole 408 and disc space 406.

Figure 31:
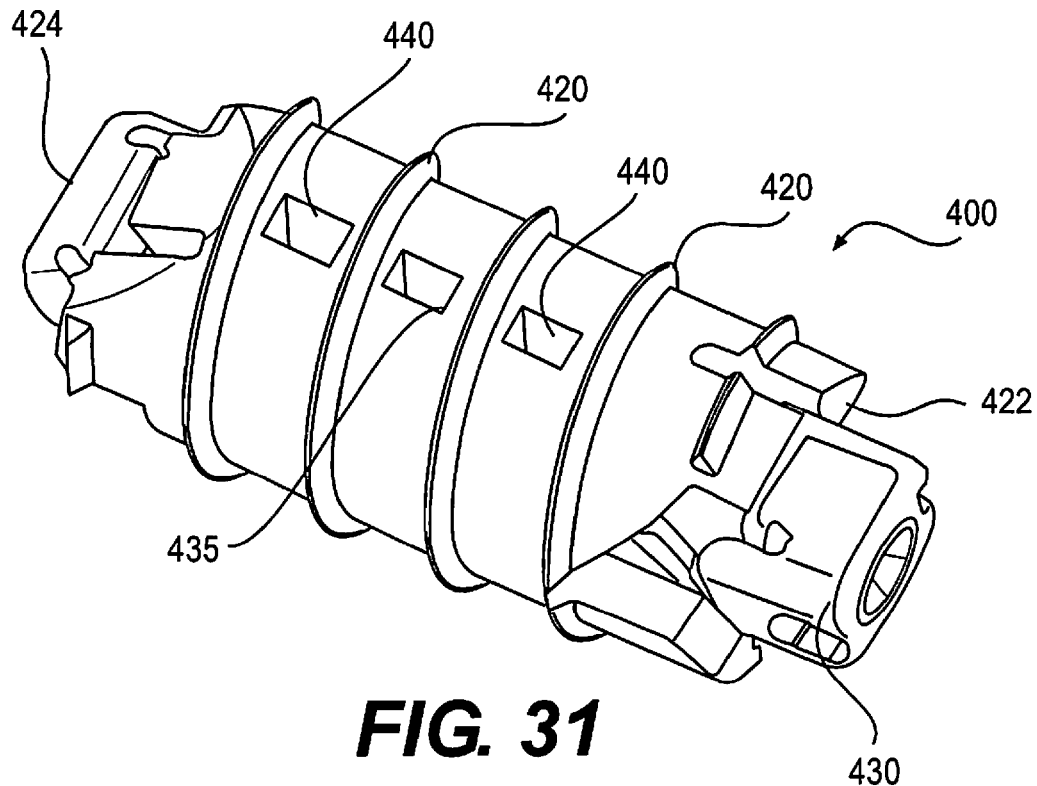
FIG. 31 illustrates a perspective view of an expandable spacer in a non-expanded state according to an exemplary embodiment of the present disclosure.
Figure 32:
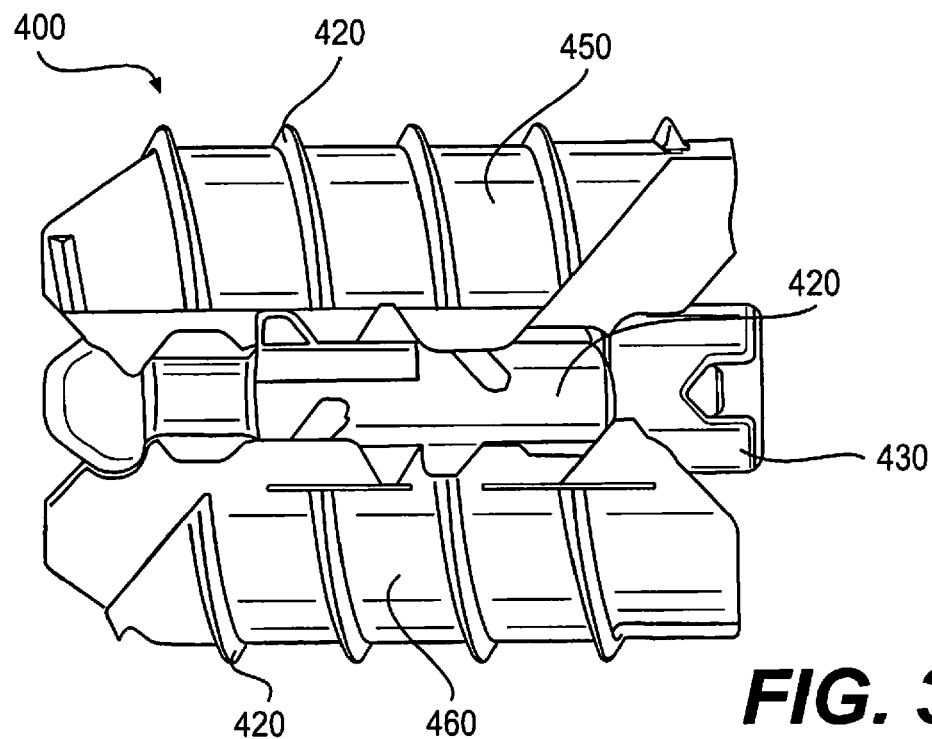
FIG. 32 illustrates a perspective view of an expandable spacer in an expanded state according to an exemplary embodiment of the present disclosure.

Referring to FIGS. 31-32, in some embodiments, the threaded expandable spacer 400 can include a distal end 424 and a proximal end 422. The nut 430 can be provided at the proximal end 422. Threads 420 can be provided along an outer periphery of the threaded expandable spacer 400. In some exemplary embodiments, the shell 435 of the threaded expandable spacer 400 has an upper endplate 450 and a lower endplate 460. The threads 420 are provided on both the upper endplate 450 and the lower endplate 460 such that they are continuous when the threaded expandable spacer 400 is in a non-expanded state (e.g., FIG. 31). One or more graft windows 440 can be provided to provide bone graft or similar bone growth inducing material to help fuse the threaded expandable spacer 400 with the vertebral bodies.

In some exemplary embodiments, the upper endplate 450 and the lower endplate 460 can move with respect to each other to expand in an expanded state (e.g., FIG. 32). The nut 430, which can be a square nut, can be connected to expansion mechanism 470 and have an upper and lower ramp that mate with opposing ramps on the inside of the endplates, as is described in U.S. Pat. No. 8,845,731, which is incorporated by reference in its entirety. With the exception of the type of endplates described in U.S. Pat. No. 8,845,731, a similar expansion mechanism can be used for expansion mechanism 470, with endplates 450 and 460. As the nut 430 is actuated (e.g., by turning the threaded shaft in a first direction), the ramps force the endplates 450 and 460 away from the center of the threaded expandable spacer 400. The nut 430 can have pins to help retain the endplates 450 and 460. When the threaded shaft is turned in a second direction (i.e., opposite the first direction), the endplates 450 and 460 can retract back to the center of the threaded expandable spacer 400 to a non-expanded state.

Figures 33, 34:
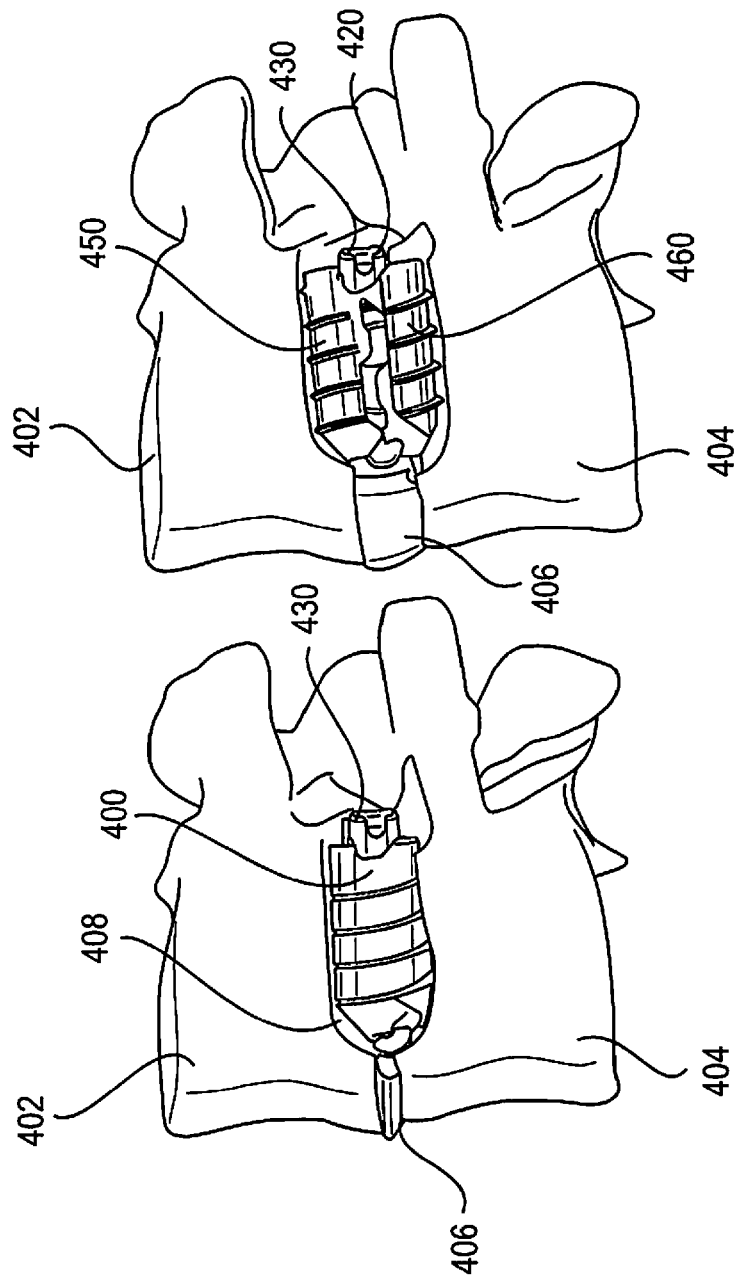
FIG. 33 illustrates a cross-section of a side view of an expandable spacer in a non-expanded state within a disc space according to an exemplary embodiment of the present disclosure.
FIG. 34 illustrates a cross-section of a side view of an expandable spacer in an expanded state within a disc space according to an exemplary embodiment of the present disclosure.

Referring to FIGS. 33-34, in some embodiments, the threaded expandable spacer 400 can be provided within a drill hole 408 in a disc space 406 between adjacent vertebral bodies 402 and 404 in a non-expanded state (e.g., FIG. 33). The threaded expandable spacer 400 can be turned so that the upper endplate 450 would expand towards the vertebral body 402 when expanded, and the lower endplate 460 would expand towards the vertebral body 404 when expanded. The nut 430 can be actuated to move the upper endplate 450 and lower endplate 460 away from the center of the threaded expandable spacer 400. The threaded expandable spacer 400 can be expanded in-situ. Graft windows 440 can be provided in both the upper endplate 450 and the lower endplate 460 to provide bone graft or similar bone growth inducing material within the threaded expandable spacer 400 to help promote fusion between the threaded expandable spacer 400 and the adjacent vertebral bodies 402 and 404. The threads 420 of the threaded expandable spacer 400 can secure the threaded expandable spacer 400 within the disc space 406 and within the vertebral bodies 402 and 404 such that posterior fixation may not be necessary, and any migration of the threaded expandable spacer 400 can be prevented. The threaded expandable spacer 400 can be threaded inside the cancellous region of the vertebral bodies, which can promote faster bone growth and yield a maximum amount of contact surface area into both adjacent vertebral bodies 402 and 404, as well as reduce the chance of backing out or migrating.

In some exemplary embodiments, in the event the threaded expandable spacer 400 needs to be repositioned or revised after being installed and expanded, the threaded expandable spacer 400 can be contracted back to the unexpanded configuration, repositioned, and expanded again once the desired positioning is achieved. To contract the threaded expandable spacer 400, an instrument can be used to rotate the actuator assembly (as described in U.S. Pat. No. 8,845,731), which can move the endplates 450 and 460 inwardly into the unexpanded position. Various different types of expansion mechanisms can be used within the endplates 450 and 460, and the present disclosure is not limited to any particular type of expansion mechanism.

Various delivery methods and devices can be used to deliver the fusion devices described in the present disclosure. For example, prior to insertion of the fusion devices described herein, the intervertebral space can be prepared. In one method of installation, a discectomy is performed where the intervertebral disc, in its entirety, can be removed. Alternatively, only a portion of the intervertebral disc can be removed. The endplates of adjacent vertebral bodies can be scraped to create an exposed end surface for facilitating bone growth across the intervertebral space. One or more endoscopic tubes can then be inserted into the disc space. The expandable fusion device can then be introduced into the intervertebral space down an endoscopic tube and seated in an appropriate position in the intervertebral disc space.

Various configurations of the expandable fusion devices are contemplated and are not limited by the embodiments described with reference to the figures. For example, various sizes, shapes and types of endplates are contemplated, and various materials can be used to construct the various parts, such as the endplates, end caps, drive plates and spikes described herein. The exemplary embodiments of the present disclosure provide various advantages, such as being able to be expanded in-situ. The intervertebral implant described herein can provide a substantially hollow portion between the endplates to allow a significant amount of bone graft or similar bone growth inducing material to be placed therein to allow maximum fusion of the bone growth inducing material within the intervertebral implant and the adjacent vertebral bodies. Although the preceding discussion only discussed having a single fusion device in the intervertebral space, it is contemplated that more than one fusion device can be inserted in the intervertebral space. It is further contemplated that each fusion device does not have to be finally installed in the fully expanded state. Rather, depending on the location of the fusion device in the intervertebral disc space, the height of the fusion device may vary from unexpanded to fully expanded. It should be noted that, as well as the height being varied from an unexpanded state to an expanded state, the fusion may be positioned permanently anywhere between the expanded state and the unexpanded state.

In some embodiments, the fusion devices described above can be accompanied with other devices, including but not limited to rods, screw (e.g., pedicle screws), plates, and other stabilization devices. In addition, while any of the devices described above can be used on a single level, a multi-level procedure can be performed using multiple similar device, or using one device with a different device. For example, it is possible to use any of the fusion devices described above in one level, while having a prosthetic implant on another level.

The foregoing merely illustrates the principles of the disclosure. Various modifications and alterations to the described embodiments will be apparent to those skilled in the art in view of the teachings herein. It will thus be appreciated that those skilled in the art will be able to devise numerous apparatuses, arrangements, manufacture and methods which, although not explicitly shown or described herein, embody the principles of the disclosure and are thus within the spirit and scope of the disclosure. The disclosures of all documents and publications cited herein are hereby incorporated herein by reference in their entireties.

What is claimed is:

1. An intervertebral implant, comprising:
 a first endplate having an upper surface and a lower surface, wherein the first endplate comprises a first side wall that extends from the first endplate; and
 a second endplate having an upper surface and a lower surface, wherein the second endplate includes a second side wall that extends from the second endplate;
 an engagement mechanism for engaging the first sidewall to the second sidewall and configured to provide a selective height between the first endplate and the second endplate; and
 a fixation member capable of engaging an adjacent vertebra,
 wherein the engagement mechanism comprises an opening for receiving the fixation member to secure the implant to the adjacent vertebra,
 wherein the first side wall and the second side wall are configured to engage one another and provide a selective height between the first endplate and the second endplate;
 wherein the first side wall and the second side wall form a substantially hollow portion substantially enclosed by the first endplate, second endplate, first side wall and the second side wall; and
 wherein the substantially hollow portion is configured to receive bone growth inducing material,
 a drive plate provided within an end cap, the drive plate comprising a first spike configured to advance from the drive plate and engage with a vertebral body for securing the intervertebral implant to a vertebral body above the first endplate, and a second spike configured to advance from the drive plate and engage with a vertebral body for securing the intervertebral implant to a vertebral body below the second endplate.

2. The intervertebral implant of claim 1, wherein the first side wall is integral with the first endplate and the second sidewall is integral with the second endplate.

3. The intervertebral implant of claim 1, wherein the engagement mechanism comprises a plurality of rails along a length of an outer portion of the first sidewall from a proximal end to a distal end and a plurality of grooves along a length of an inner portion of the second sidewall from a proximal end to a distal end for selective engagement with the one or more rails.

4. The intervertebral implant of claim 3, wherein the first sidewall comprises a wall extending from a first side, a second opposing side and a distal end of the first endplate, and the second sidewall comprises a wall extending from a first side, a second opposing side and a distal end of the second endplate.

5. The intervertebral implant of claim 4, further comprising:
 an opening between a proximal end of the first endplate and a proximal end of the second endplate configured to allow placement of an implant holder therein.

6. The intervertebral implant of claim 5, further comprising:
 an implant holder interface provided along an outer portion of the second sidewall at opposing ends and configured to secure the intervertebral implant to an implant holder.

7. The intervertebral implant of claim 6, further comprising:
 an end cap interface provided along an outer portion of the second sidewall at opposing ends.

8. The intervertebral implant of claim 7,
wherein the end cap is configured to be secured to the end cap interface of the second sidewall engaging a wall of the lower surface of the first endplate and the upper surface of the second endplate, the end cap configured to prevent displacement of the first endplate with respect to the second endplate.

9. The intervertebral implant of claim 8, wherein the end cap seals the opening between the proximal end of the first endplate and the proximal end of the second endplate.

10. The intervertebral implant of claim 9, further comprising:
a securing mechanism in the end cap for securing the intervertebral implant to a vertebral body above the first endplate and a vertebral body below the second endplate.

11. The intervertebral implant of claim 3, wherein the substantially hollow portion is configured for placement of a cam, and configured to displace and engage the engagement mechanism as the cam is rotated.

12. The intervertebral implant of claim 1, wherein the first and second spikes are configured to advance as a driver engaged with the drive plate is turned.

13. The intervertebral implant of claim 1, further comprising:
one or more slots between the upper surface of the first endplate to the lower surface of the first endplate configured to allow fusion of bone growth inducing material within the intervertebral implant and a vertebral body above the first endplate; and
one or more slots extending from the upper surface of the second endplate to the lower surface of the second endplate configured to allow fusion of bone growth inducing material within the intervertebral implant and a vertebral body below the second endplate.

14. The intervertebral implant of claim 1, wherein an upper surface of the first endplate comprises texturing for engaging with a vertebral body and a lower surface of the second endplate comprises texturing for engaging with a vertebral body.

15. An intervertebral implant, comprising:
an upper endplate having a proximal end, a distal end, a first side and an opposing second side;
a lower endplate having a proximal end, a distal end, a first side and an opposing second side;
a first sidewall extending along the first side, distal end and second side of the upper endplate towards the lower endplate;
a second sidewall extending along the first side, distal end and second side of the lower endplate towards the upper endplate; and
an engagement mechanism for selective engagement of the first sidewall with the second sidewall configured to provide a selective distance between the upper endplate and the lower endplate, the engagement mechanism comprising an opening for receiving a fixation member to secure the implant to an adjacent vertebra;
a fixation member, the fixation member received in the opening in the engagement member to engage the adjacent vertebra
wherein the upper endplate, lower endplate, first sidewall and second sidewall partially enclose a substantially hollow portion configured to receive bone growth inducing material therein,
an end cap secured to the second sidewall engaging a wall of the upper endplate and the lower endplate, wherein a first spike configured to advance from the end cap and engage with a vertebral body for securing the intervertebral implant to a vertebral body above the first endplate, and a second spike configured to advance from the end cap and engage with a vertebral body for securing the intervertebral implant to a vertebral body below the second endplate.

16. The intervertebral implant of claim 15, wherein:
the end cap configured to retain a selected height between the upper endplate and the lower endplate and seal an opening between the proximal ends of the upper endplate and the lower endplate.

17. The intervertebral implant of claim 15, further comprising:
one or more slots in the upper endplate configured to allow fusion of bone growth inducing material within the intervertebral implant and a vertebral body above the upper endplate; and
one or more slots in the lower endplate configured to allow fusion of bone growth inducing material within the intervertebral implant and a vertebral body below the lower endplate.

18. The intervertebral implant of claim 15, wherein the engagement mechanism comprises a plurality of rails along a length of an outer portion of the first sidewall from a proximal end to a distal end and a plurality of grooves along a length of an inner portion of the second sidewall from a proximal end to a distal end for selective engagement with the one or more rails.

* * * * *